(12) United States Patent
Bailey et al.

(10) Patent No.: US 8,552,240 B2
(45) Date of Patent: *Oct. 8, 2013

(54) PROCESS FOR PRODUCING PROPYLENE

(75) Inventors: Craig Bailey, Beverley (GB); Leslie William Bolton, Fleet (GB); Benjamin Patrick Gracey, Hull (GB); Michael Keith Lee, Hull (GB); Stephen Roy Partington, Beverley (GB)

(73) Assignee: BP Chemicals Limited, Middlesex (GB)

( * ) Notice: Subject to any disclaimer, the term of this patent is extended or adjusted under 35 U.S.C. 154(b) by 354 days.

This patent is subject to a terminal disclaimer.

(21) Appl. No.: 12/085,704

(22) PCT Filed: Nov. 22, 2006

(86) PCT No.: PCT/GB2006/004351
§ 371 (c)(1),
(2), (4) Date: May 29, 2008

(87) PCT Pub. No.: WO2007/063280
PCT Pub. Date: Jun. 7, 2007

(65) Prior Publication Data
US 2009/0281362 A1   Nov. 12, 2009

(30) Foreign Application Priority Data
Nov. 29, 2005  (EP) ..................... 05257321

(51) Int. Cl.
*C07C 1/24* (2006.01)
(52) U.S. Cl.
USPC ........... 585/639; 585/322; 585/408; 585/469; 585/640; 585/733; 568/909
(58) Field of Classification Search
USPC ................. 585/322, 408, 469, 639, 640, 698, 585/733; 568/909
See application file for complete search history.

(56) References Cited

U.S. PATENT DOCUMENTS 3,529,033 A * 9/1970 Frilette et al. ................ 585/640
4,232,179 A  11/1980 Valladares Barrocas et al.
(Continued)

FOREIGN PATENT DOCUMENTS

EP   0 379 803 A1   8/1990
SU       376113    6/1973

OTHER PUBLICATIONS

Onfroy, T., et al; "Acidity, Surface Structure, and Catalytic Performance of WO$_x$ Supported on Monoclinic Zirconia"; *J. Phys. Chem. B.*; vol. 109, No. 8, pp. 3345-3354 (2005).
Office Action issued in Chinese Application No. 200680051964.2 (PCT/GB2006/004351), dated Apr. 22, 2011, 16 pgs. (now Chinese Patent No. CN 101336217A).
Office Action issued in Russian Patent Application No. 2008 126 388, dated May 19, 2010, 8 pgs. (now Russian Patent No. RU 2415832 C2).

*Primary Examiner* — In Suk Bullock
*Assistant Examiner* — Sharon Pregler
(74) *Attorney, Agent, or Firm* — Nixon & Vanderhye

(57) ABSTRACT

Process for producing propylene from a propanol feedstock A2 by reacting the propanol feedstock A2 in a vapor phase dehydration reactor wherein the propanol is convened at a temperature comprised between 160 and 270° C. and at a pressure of above 0.1 MPa but less than 4.5 MPa, into a product stream B2 containing propylene, propyl ethers, water and unconverted and/or isomerized propanols, cooling the product stream B2, disengaging the cooled product stream B2 in a separation unit to give a first stream C2 containing propylene and propyl ethers, and a second product stream D2 containing water, propyl ethers and unconverted and/or isomerized propanols, feeding the product stream D2 to a dewatering unit wherein the water stream F2 is separated from the propyl ethers and unconverted and/or isomerised propanols stream E2, recycling the stream E2 into the dehydration reactor, cooling the product stream C2, feeding the cooled product stream C2 to a purification unit wherein the propyl ethers stream G2 is separated from the propylene stream H2, and optionally, recycling the propyl ethers stream G2 to either the dewatering unit or directly to dehydration reactor.

28 Claims, 1 Drawing Sheet

(56) References Cited

U.S. PATENT DOCUMENTS

| | | |
|---|---|---|
| 4,396,789 A | 8/1983 | Barrocas et al. |
| 4,398,050 A | 8/1983 | Hofstadt et al. |
| 4,476,338 A * | 10/1984 | Chang et al. ............ 585/322 |
| 4,727,214 A | 2/1988 | Uytterhoeven et al. |
| 5,475,183 A | 12/1995 | Araki et al. |
| 2003/0027712 A1 * | 2/2003 | Vaughn et al. ............ 502/63 |

* cited by examiner

PROCESS FOR PRODUCING PROPYLENE

This application is the U.S. national phase of International Application No. PCT/GB2006/004351 filed 22 Nov. 2006 which designated the U.S. and claims priority to 05257321.9 filed 29 Nov. 2005, the entire contents of each of which are hereby incorporated by reference.

The present invention relates to a process for file production of propylene from a feedstock comprising propanol.

BACKGROUND OF THE INVENTION

Olefin(s) have traditionally been produced by steam or catalytic cracking of hydrocarbons. However, inevitably as oil resources decrease the price of oil will continue to increase; making light olefin(s) production a costly process. Thus mere is an ever-growing need for non-petroleum routes to produce $C_2+$ olefin(s), essentially ethylene and propylene. Such olefin(s) are useful starting materials for numerous chemical products including polymeric products such as polyethylene and polypropylene.

In recent years the search for alternative materials for C2+ olefin(s) production has led to the use of alcohols such as methanol, ethanol and higher alcohols. The said alcohols may be produced by the fermentation of, for example, sugars and/or cellulosic materials.

Alternatively, alcohols may be produced from synthesis gas (also known as "syngas"). Synthesis gas refers to a combination of hydrogen and carbon oxides produced in a synthesis gas plant from a carbon source such as natural gas, petroleum liquids, biomass and carbonaceous materials including coal, recycled plastics, municipal wastes, or any organic material. Thus, alcohol and alcohol derivatives may provide non-petroleum based routes for the production of olefin(s) and other related hydrocarbons.

Generally, the production of oxygenates, primarily methanol, takes place via three process steps. The three process steps are: synthesis gas preparation, methanol synthesis, and methanol purification. In the synthesis gas preparation step, an additional stage maybe employed by where the feedstock is treated, e.g. the feedstock is purified to remove sulfur and other potential catalyst poisons prior to being converted into synthesis gas. This additional stage can also be conducted after syngas preparation, e.g. when coal or biomass is employed.

Processes for producing mixtures of carbon oxide(s) and hydrogen (synthesis gas) are well known. Each has its advantages and disadvantages and the choice of using a particular reforming process is dictated by economic and available feed stream considerations, as well as by the desired mole ratio of H2:CO in the feedstock resulting from the reforming reaction. The synthesis gas may be prepared using any of the processes known in the art including partial oxidation of hydrocarbons, steam reforming, gas heated reforming, microchannel reforming (as described in, for example, U.S. Pat. No. 6,284,217), plasma reforming, autothermal reforming and any combination thereof. A discussion of these synthesis gas production technologies is provided in "Hydrocarbon Processing" V 78, N. 4, 87-90, 92-93 (April 1999) and "Petrole et Techniques", N. 415, 86-93 (July-August 1998). It is also known that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187-196. Alternatively, the synthesis gas may be obtained by short contact time catalytic partial oxidation of hydrocarbonaceous feedstocks as described in EP 0303438. Typically synthesis gas is obtained via a "Compact Reformer" process as described in "Hydrocarbon Engineering", 2000, 5, (5), 67-69; "Hydrocarbon Processing", 79/9, 34 (September 2000); "Today's Refinery", 15/8, 9 (August 2000); WO 99/02254; and WO 200023689.

Typically, for commercial syngas production the pressure at which the synthesis gas is produced ranges from approximately 20 to 75 bar and the temperature at which the synthesis gas exits the reformer ranges from approximately 700 DEG C. to 1100 DEG C. The synthesis gas contains a molar ratio of hydrogen to carbon oxide—which is dependent on the syngas feedstock—ranging from 0.8 to 3.

Alcohol synthesis from syngas requires a H2:CO molar ratio which is typically between 1:1 and 2:1.

The applicants believe that the reaction of producing alcohol, such as ethanol, from synthesis gas can be written as so: 2 CO+4H2→EtOH+H2O reaction stoichiometry 2:1 However, in addition to this the water gas shift reaction can also readily occur and thus the equilibrium under typical alcohol synthesis conditions strongly favours carbon dioxide and hydrogen production.

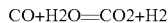

So the overall alcohol synthesis can be written as so: 3 CO+3H2→EtOH+CO2 reaction stoichiometry 1:1

In addition to this the water gas shift reaction allows CO2 and H2 to substitute for CO. So the required molar syngas ratio for alcohol synthesis can be written in terms of (H2−CO2):(CO+CO2) and in this case the required ratio is 2.

However, the H2:CO molar ratio used in practice is typically higher due to by-product formation, such as alkanes. The synthesis gas preparation, also know man those stated above, as reforming may take place in a single-step wherein all of the energy consuming and generating reforming reactions are accomplished. For example, in a single tubular steam reformer the reaction is overall endothermic whereas in autothermal reforming combustion of some of the feed and product is used to balance the heat duty. The single-step stream reformer usually results in the production of surplus hydrogen. In a preferred alternative, the synthesis gas preparation may take place in a two-step reforming process wherein the primary reforming in a tubular steam reformer is combined with an oxygen-fired secondary reforming step which if used in isolation produces a synthesis gas with a deficiency in hydrogen. With this combination it is possible to adjust the synthesis gas composition used, in order to obtain the most suitable composition for methanol synthesis. As an alternative, autothermal reforming results in a simplified process scheme with a lower capital cost. Autothermal reforming is where a stand-alone, oxygen-fired reformer first produces a hydrogen deficient synthesis gas, and then removes a least a portion of the carbon dioxide present, in order to obtain the desired molar ratio of hydrogen to carbon oxides.

The reaction from synthesis gas to oxygenates such as methanol is an exothermic equilibrium limited reaction. The conversion per pass to methanol is favored by low temperatures but a balance between rate and conversion must be maintained for economic considerations. It also requires high pressures over a heterogeneous catalyst, as the reactions which produce methanol exhibit a decrease in volume. As disclosed in U.S. Pat. No. 3,326,956, low-pressure methanol synthesis is based on a copper oxide-zinc oxide-alumina catalyst that typically operates at a nominal pressure of 5-10 MPa and temperatures ranging from approximately 150 DEG C. to 450 DEG C. over a variety of catalysts, including CuO/ZnO/Al2 O3, CuO/ZnO/Cr2 O3, ZnO/Cr2 O3, Fe, Co, Ni, Ru, Os, Pt, and Pd. Catalysts based on ZnO for the production of methanol and dimethyl ether are preferred. The low-pressure, copper-based methanol synthesis catalyst is commercially available from suppliers such as BASF, ICI Ltd. of the United Kingdom, and Haldor-Topsoe. Methanol yields from copper-based catalysts are generally over 99.5% of the converted CO+CO2 present Water is a known by-product of the conversion of the synthesis gas to oxygenates. A paper entitled, "Selection of Technology for Large Methanol Plants," by Helge Holm-Larsen, presented at the 1994 World Methanol Conference, Nov. 30-Dec. 1, 1994, in Geneva, Switzerland, and herein incorporated by reference, reviews the developments in methanol production and shows how further reduction in costs of methanol production will result in the construction of very large plants with capacities approaching 10,000 metric tonnes per day.

U.S. Pat. No. 4,543,435 discloses a process for converting an oxygenate feedstock comprising methanol, dimethyl ether or the like in an oxygenate conversion reactor into liquid hydrocarbons comprising C2-C4 olefin(s) and C5+ hydrocarbons. The C2-C4 olefin(s) are compressed to recover an ethylene-rich gas. The ethylene-rich gas is recycled to the oxygenate conversion reactor. U.S. Pat. No. 4,076,761 discloses a process for converting oxygenates to gasoline with the return of a hydrogen-rich gaseous product to a synthesis gas plant or the oxygenate conversion reaction zone. U.S. Pat. No. 5,177,114 discloses a process for the conversion of natural gas to gasoline grade liquid hydrocarbons and/or olefin(s) by converting the natural gas to a synthesis gas, and converting the synthesis gas to crude methanol and/or dimethyl ether and further converting the crude methanol/dimethyl ether to gasoline and olefin(s). International Patent Application No. 93/13013 to Kvisle et al. relates to an improved method for producing a silicon-alumino-phosphate catalyst which is more stable to deactivation by coking. The patent discloses that after a period of time, all such catalysts used to convert methanol to olefin(s) (MTO) lose the active ability to convert methanol to hydrocarbons primarily because the microporous crystal structure is coked; that is, filled up with low volatility carbonaceous compounds which block the pore structure. The carbonaceous compounds can be removed by conventional methods such as combustion in air.

EPO publication No. 0 407 038A1 describes a method for producing dialkyl ethers comprising feeding a stream containing an alkyl alcohol to a distillation column reactor into a feed zone, contacting the stream with a fixed bed solid acidic catalytic distillation structure to form the corresponding dialkyl ether and water, and concurrently fractionating the ether product from the water and unreacted materials.

U.S. Pat. No. 5,817,906 describes a process for producing light olefin(s) from a crude oxygenate feedstock comprising alcohol and water. The process employs two reaction stages. Firstly, the alcohol is converted using reaction with distillation to an ether. The ether is men subsequently passed to an oxygenate conversion zone containing a metal aluminosilicate catalyst to produce a light olefin stream.

There is a well known chemistry that can be employed to produce olefin(s) from alcohol(s), i.e. the Methanol to olefin(s)—MTO—process (as described in Handbook of Petroleum refining processes third edition, Chapter 15.1 editor R. A. Meyers published by McGraw Hill).

This said MTO Process can be described as the dehydrative coupling of methanol to olefin(s). This mechanism is thought to proceed via a coupling of C1 fragments generated by the acid catalysed dehydration of methanol, possibly via a methyloxonium intermediate. However the main disadvantage of the said MTO process is that a range of olefin(s) are co-produced together with aromatic and alkane by-products, which in turn makes it Very difficult and expensive to recover the desired olefin(s) at high purity.

Molecular sieves such as the microporous crystalline zeolite and non-zeolitic catalysts, particularly silicoaluminophosphates (SAPO), are known to promote the conversion of oxygenates by methanol to olefin (MTO) chemistry to hydrocarbon mixtures. Various patents describe the various types of these catalysts mat may be used in this process, such as: U.S. Pat. Nos. 3,928,483, 4,025,575, 4,252,479 (Chang et al); U.S. Pat. No. 4,496,786 (Santilli et al.); U.S. Pat. No. 4,547,616 (Avidan et al.); U.S. Pat. No. 4,677,243 (Kaiser); U.S. Pat. No. 4,843,183 (Inui); U.S. Pat. No. 4,499,314 (Seddon et al.); U.S. Pat. No. 4,447,669 (Harmon et al.); U.S. Pat. No. 5,095, 163 (Barger); U.S. Pat. No. 5,191,141 (Barger); U.S. Pat. No. 5,126,308 (Barger); U.S. Pat. No. 4,973,792 (Lewis); and U.S. Pat. No. 4,861,938 (Lewis).

The MTO reaction has a high activation energy, possibly in the methanol or dimethyl ether activation step so in order to achieve reasonable rates mere is often a need for high temperatures e.g. 300-450° C. However, unfortunately operating at these said high temperatures leads to major problems such as catalyst deactivation, coking and significant by-product formation. In order to minimize these problems the reactions may be operated at lower temperatures, but this necessitates larger reactors in addition to a large expensive recycle of intermediates and reactants.

Another major disadvantage associated with the MTO process is that the aromatic and alkane by-products are co-produced together with the olefin(s) and are both difficult and expensive to separate from the desired products, e.g. separating ethylene and ethane is an expensive process.

These and other disadvantages of the prior art show that there is a need for an improved and/or alternative process for the production of C2 and C3 olefins from alcohols.

SUMMARY OF THE INVENTION

The solution to these and other disadvantages is provided by the present invention, which relates specifically to a new non-MTO process which proceeds via the dehydration of propanol into olefins. This dehydration reaction is characterized in that carbon-carbon double bonds are formed by elimination of water only and does not include the coupling of carbon fragments as is the case in MTO chemistry. It should be noted that for the dehydration of propanol, by-products are formed. These can be formed by coupling of alkyl fragments e.g. acid catalysed olefin oligomerisation, such as:
2 propylene→Hexene The by-products can also be formed by alcohol dehydrogenation, e.g.
Ethanol→Acetaldehyde+H2 (J. Catalysis 1989, 117, pp 135-143 Y. Matsumura, K. Hashimoto and S. Yoshida).

The state of the hydrogen liberated may not be as free hydrogen but as chemisorbed hydrogen. Of particular relevance is the transfer, hydrogenation reaction e.g.
Ethylene+H2→ethane
2 Ethanol→Acetaldehyde+ethane+water The formation of same carbon number alkanes is known to add significantly to the complexity and cost of producing purified olefins for polymer manufacture. For example the industrially practiced catalytic cracking of hydrocarbon feedstocks to produce olefins for polymer manufacture is a capitally intensive process with a significant proportion of the cost involved in same number olefin and alkane separation. That is separation of ethane from ethylene and propane from propylene (as described in Handbook of Petroleum refining processes third edition, Chapter 3 editor R. A. Meyers published by McGraw Hill). This is also a disadvantage for the MTO process, (Ibid chapter 15.1). Dehydration of ethanol to ethylene has been commercially practiced in places such as Brazil, and India, albeit at a small scale. The reported reaction conditions are such that high conversion per pass to olefin is achieved at e.g. 1-2 barg, >350 C. It is a high selectivity process but produces unacceptable levels of alkanes for direct use in the preparation of polyethylene. Acceptable levels are often quoted as less than 500 ppm combined ethane and methane. Current practice of dehydration leads to olefins which need expensive purification before use in current polymerization processes, as is also the case with MTO.

U.S. Pat. No. 5,475,183 describes a process for producing light olefins by dehydrating lower alcohols having 2-4 carbon atoms on a alumina catalyst in the vapour phase. The typical reaction conditions given in the examples are 300-400 C at 8 to 18 Barg with reported olefin selectivities between 65 and 97%.

GB Pat No 2094829 describes how ethylene can be produced in a plurality of vapour phase adiabatic reactors with parts of the liquid products containing unconverted alcohol being recycled. The reaction conditions are described as the feed charge is at 400-520 C. and a pressure 19-39 barg. The outlet product being kept at least 18 barg prior to being cryogenically purified. No examples were given of the predicted selectivity. U.S. Pat. No. 4,232,179 also describes how ethanol can be dehydrated in adiabatic reactors. The examples, with silica/alumina, and alumina show that the ethane content in the ethylene product is above 923-100000 ppm wt on ethylene. This is unacceptable for polyethylene production without additional purification.

DD Pat No 245866 describes how C2 to C4 olefins can be obtained from syngas-derived alcohol mixtures by vapour phase treatment with a zeolite catalyst between 300-500 C. and 200-1000 kPa. Analysis of the examples has shown that significant conversion to C5 and higher hydrocarbons occurred. The examples describe the dehydration of mixtures of C1 to C7 alcohols. Example 1 describes the dehydration of a mixture of 76% methanol, 7.1% ethanol, 4.3% ethanol, 0.5% isopropanol, 4.3% n-propanol, 3.9% iso-butanol, 2% butanols, 2.1% amyl alcohol, 0.9% hexanols, 0.2% heptanols+balance other oxygenates to give 143.2 g ethylene, 96.8 g propene, 77.9 g butene, 174.3 g C5+ hydrocarbons. Clearly significant conversion of lower carbon moieties to higher carbon fragments is occurring on the modified zeolite catalyst.

U.S. Pat. No. 4,398,050 describes the synthesis of a mixed alcohol stream and purification to give a mixture of ethanol and propanol which is subsequently dehydrated at 0.5-1 bar, 350-500 C. (example 1). The primary claim mentions the removal of methanol prior to dehydration, but not the removal of C4 and higher alcohols.

U.S. Pat. No. 4,423,270 describes the atmospheric pressure vapour phase dehydration of ethanol over a supported phosphoric acid catalyst with additional water and an alkyl substituted phosphoric acid. The reaction temperatures employed are between 300-400 C. and the experiments were conducted at atmospheric pressure in a glass tube. The reported yields of ethylene ranged from 88-101%, no details of by-product formation was disclosed.

U.S. Pat. No. 4,727,214 describes the dehydration of ethanol over a crystalline aluminosilicate zeolite. The conditions claimed are between 1 and 10 bar and 126 and 526 C. Details of by-product formation are supplied to one decimal place and a selectivity to ethylene of 100% is reported. It is, however unclear from the patent if material suitable for polymer grade ethylene can be made without additional purification for removal of ethane.

Limited experimental information is available for n-propanol dehydration (Journal of Catalysis 169, 67-75 (1997) G. Larsen et al, J. Phy. Chem. B 109/8 3345-3354), we have found that the dehydration proceeds in a similar manner to that reported for ethanol, with similar by-product formation e.g. alkanes, aldehydes, ketones, oligomers. The rate of oligomer formation is however more significant.

The present invention relates to a process for the production of propylene from propanol.

Figure 1:
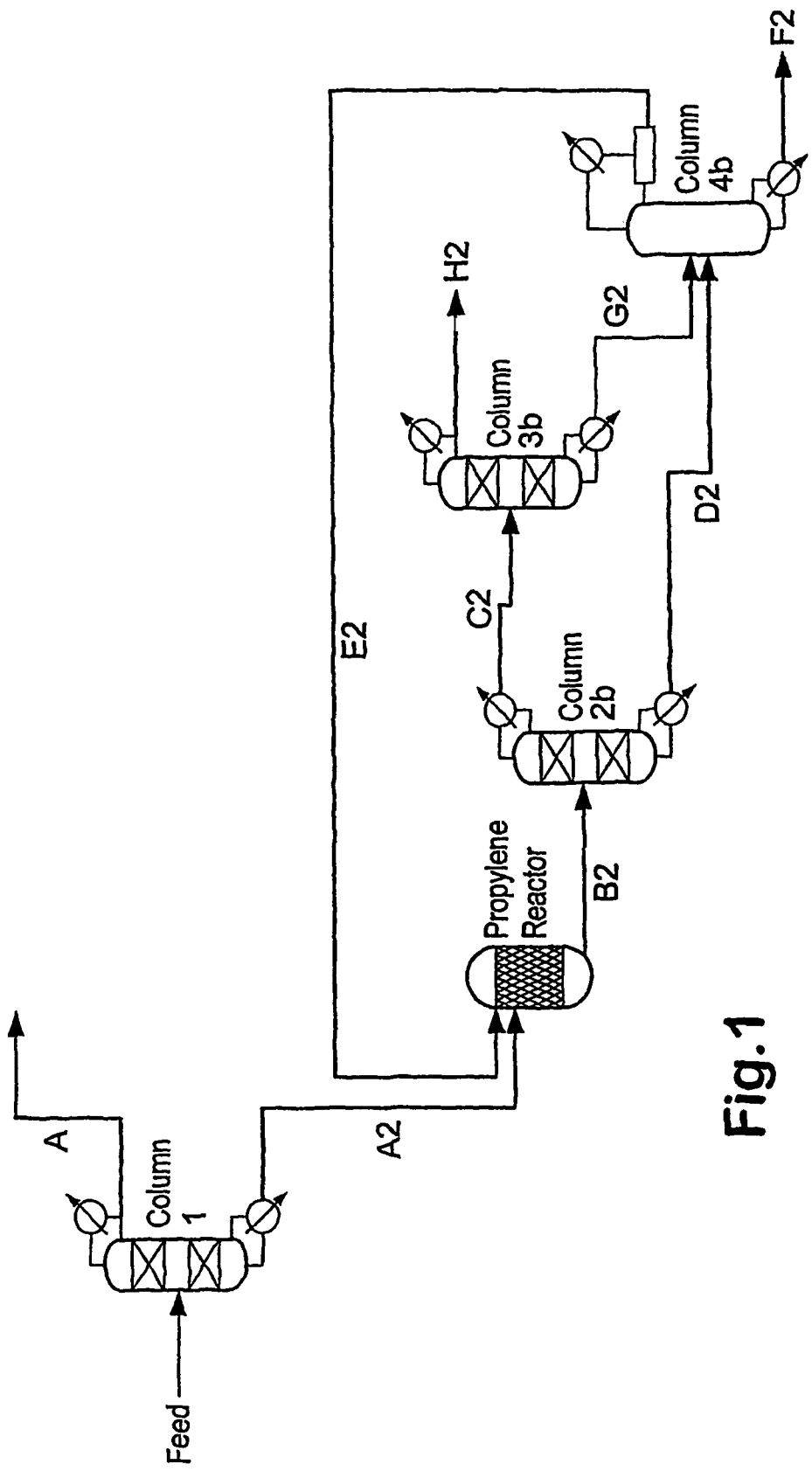
FIG. 1 represents one embodiment of a process scheme according to the present invention. This said embodiment comprises optional and/or preferred process steps according to the present invention. The letter references in FIG. 1 correspond to those used in the present description and appending claims.

The present invention relates to a process for the production of propylene from a propanol feedstock A2 characterised by the following steps;

1. the propanol feedstock A2 is reacted in a vapour phase reactor wherein the propanol is converted into a product stream B2 comprising propylene, propyl ethers, water and unconverted and/or isomerised propanols,
2. the said product stream B2 is cooled,
3. the said cooled product stream B2 is disengaged in a separation unit to give a first stream C2 comprising propylene and propyl ethers, and a second product stream D2 comprising water, propyl ethers and unconverted and/or isomerised propanols,
4. the said product stream D2 is fed to a dewatering unit wherein the water stream F2 is separated from the propyl ethers and unconverted and/or isomerised propanols stream E2,
5. the said stream E2 is recycled into the dehydration reactor of step 1,
6. the said product stream C2 is cooled,
7. the said cooled product stream C2 is fed to a purification unit wherein the propyl ethers stream G2 is separated from the propylene stream H2, and
8. optionally, the propyl ethers stream G2 is recycled to either the dewatering unit of step 4 or directly to dehydration reactor of step 1.

According to a preferred embodiment, the present invention provides a process for the conversion of hydrocarbon to propylene wherein the propanol feed A2 used in the hereabove step 1 come from the separation of a mixed ethanol and propanol oxygenates feedstock.

According to another preferred embodiment, the present invention provides a process for the conversion of hydrocarbons to propylene comprising the steps of a. converting hydrocarbons in a syngas reactor into a mixture of carbon oxide(s) and hydrogen,
b. converting the said mixture of carbon oxide(s) and hydrogen from step (a) in the presence of a particulate catalyst in a reactor under a temperature comprised between 200 and 400° C. and a pressure of 5 to 20 MPa into a feedstock comprising propanol,
c. using at least part of said feedstock comprising propanol as the propanol feed A2 and proceeding according to steps 1 to 8 hereinabove and according to the present invention to produce the said propylene.

Any hydrocarbon-containing feed stream that can be converted into a feedstock comprising carbon monoxide and hydrogen, most preferably a synthesis gas (or "syngas"), is useful in the processes of the invention.

The hydrocarbon feedstock used for syngas generation is preferably a carbonaceous material, for example biomass, plastic, naphtha, refinery bottoms, smelter off gas, municipal waste, coal, coke and/or natural gas; coal and natural gas being the preferred carbonaceous material and most preferably the hydrocarbon feedstock is natural gas.

Feedstocks comprising carbon monoxide and hydrogen, e.g. synthesis gas may undergo purification prior to being fed into any of the reaction zones. Synthesis gas purification may be carried out by processes known in the art. See, for example, Weissermel, K. and Arpe H.-J., Industrial Organic Chemistry, Second, Revised and Extended Edition, 1993, pp. 19-21.

According to the present invention the method for the production of olefins from alcohols proceeds via the dehydration of the said alcohols. These dehydration reactions are distinguished from the aforementioned MTO process in mat although no coupling of carbon fragments is required in the dehydration process a C—C double bond is formed during the elimination of water and as a result high selectivity can be achieved. In general the conditions employed in the MTO process are much more severe than those employed in alcohol dehydration described herein.

The dehydration of the feedstock according to the present invention is believed (Chem. Eng Comm. 1990 vol 95 pp 27-39 C. L. Chang, A. L. DeVera and D. J. Miller) to proceed by either the direct dehydration to olefin(s) and water;

or via an ether intermediate;

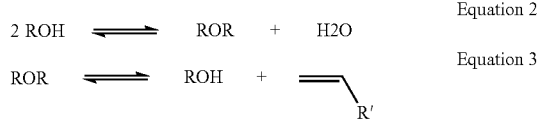

where R is a propyl group. R' is a methyl group. The direct conversion of the ether to two moles of olefin and water has also been reported (Chem. Eng. Res and Design 1984 Vol 62 pp 81-91).

All of the reactions shown above are typically catalysed by Lewis and/or Bronsted acids. Equation 1 shows the endothermic direct elimination of alcohol to olefin(s) and water; competing with Equation 1 are Equations 2 and 3 i.e. the exothermic etherification reaction (Equation 2), and the endothermic elimination of ether(s) to produce olefin(s) and alcohol (Equation 3). However the dehydration reaction of alcohols to olefin(s) is overall said to be endothermic.

As mentioned hereabove, the process according to the present invention preferably starts with an oxygenated feedstock comprising ethanol and propanol, for example a mixture of ethanol and n-propanol and/or iso-propanol.

Said oxygenate feedstock can comprise homo and mixed ethers of these alcohols, for example diethyl ether, n-propyl ether, ethyl n-propyl ether, ethyl isopropyl ether, n-propyl isopropyl ether and iso-propyl ether.

The oxygenates feedstock preferably comprises as alcohols a mixture of ethanol and n-propanol only.

According to the present invention, the molar ratio of ethanol to n-propanol in the oxygenates feedstock to be separated into the propanol feed A2 is preferably higher than 1:2 but lower than 20:1 and is more preferably higher than 1:1 but lower man 10:1, most preferably higher man 2:1 and lower than 5:1.

According to a preferred embodiment of the present invention, the oxygenates feedstock and/or die feedstock A2 has a iso-propanol content of less than 5 wt %, preferably less than 1 wt %, most preferably less than 0.1 wt % and ideally contains no iso-propanol.

A preferred characterizing feature according to the present invention is that the oxygenates feedstock and/or the feedstock A2 comprises a total C3+ alcohols (C3+ alcohols being defined as alcohols having at least 4 carbon atoms, e.g. n-butanol, iso-butanol, pentanol) content of less man 5 wt %, preferably less than 1 wt %, most preferably less than 0.1 wt % and ideally contains no C3+ alcohols. Conventional distillation can be used according to the present invention in order to reduce/eliminate the C3+ from the corresponding feedstock.

Indeed the Applicants have unexpectedly discovered that the presence of C3+ alcohols to be detrimental towards the olefin(s) production process of the present invention, e.g. the Applicants believe that they are responsible for an increase in alkane make during the olefin production.

Another preferred embodiment according to die present invention is that the oxygenates feedstock and/or die feedstock A2 comprises less than 5 wt % of methanol, preferably less man 2 wt % of methanol and most preferably less than 0.5 wt % of methanol and ideally there is no methanol. Corresponding advantages may accrue from eliminating methanol, i.e.
 (i) Prevention of dimethyl ether formation—DME is hard to separate from propylene and ethylene compared to diethyl ether
 (ii) Prevention of MTO chemistry
 (iii) Prevention of alkylation of olefins e.g. propylene to butane
 (iv) Prevention of the formation of methyl ethyl ether (which is harder to separate from ethylene)
 (v) Less waste
 (vi) Lower toxicity
 (vii) Lower vapour pressure—easier to ship
 (viii) A better C:O ratio in the feedstock for shipping i.e. less water production Conventional distillation can be used according to the present invention in order to reduce/eliminate the methanol and C3+ alcohols from the corresponding feedstock.

When a mixed ethanol and propanol feedstock is obtained from hereinabove step b), men a separation of the ethanol and propanol feedstock into an ethanol feedstock A and a propanol feedstock A2 is preferably performed. Said separation is preferably performed in a conventional distillation column.

The separation is preferably performed in such a way that the resulting propanol feedstock A2 comprises less than 5 wt % of ethanol (e.g. less than 1 wt % of ethanol; e.g. less than 0.1 wt % of ethanol; e.g. A2 contains no ethanol). The preferred reaction conditions of the vapour phase dehydration according to step 1 of the present invention are such that moderate conversion to olefin occurs in the reactor. The liquid product stream after olefin removal comprises mostly unreacted alcohols, ethers and water. It is preferred to recycle the major portion of the alcohols and ethers to the dehydration reactor after water by-product removal. As indicated hereabove, propanol can exist as two isomers n-propanol and iso-propanol; these isomers can inter convert under the said reaction conditions, hence the alcohol recycle stream may contain some isopropanol in addition to unreacted ethanol and n-propanol. This said isomerisation can also affect the compounds present in the ether proportion of the recycle stream. For the purpose of the present invention and appending claims, moderate conversion of the propanol feedstock A2 into propylene means that 10 to 80%, more preferably 20 to 60%, of the said propanol is converted per pass. Where "conversion" is defined as being, the ratio between the number of moles of propylene produced, versus, the number of moles of propanol together with the number of moles of propanol derived fragments in ethers (as defined by the following paragraph) mat are fed into the said vapour phase dehydration reactor(s).

According to the present invention, for the propylene generating reactor some propanol derived ether(s) such as di-n-propyl ether, n-propyl isopropyl ether and di-iso-propyl ether, are produced during the dehydration stage. It is preferred according to the present invention to proceed with an additional separation stage; thus, preferably at least 80 wt %; more preferably at least 90 wt %; most preferably at least 99 wt %; even more preferably at least 99.9 wt % of the ether(s) are separated from the olefin(s). At least part—preferably all—of the ether(s) separated are then preferably recycled into the vapour phase dehydration reactor(s).

According to an embodiment of the present invention at least part, preferably all of the said ether recycle is pre-mixed with the fresh propanol feed (stream A2) prior to entering the vapour phase dehydration reactor of step 1.

The formation of ethers is thermodynamically favorable. This ether formation facilitates separation of water from the recycle. Ethanol, n-propanol and iso-propanol are all fully or significantly water miscible and readily form water azeotropes, which thus hinders the separation of water, a by-product of the reaction, from the recycle streams. However, the formation of ethers, such as diethyl ether and di-n-propyl ether (which both have a limited water miscibility and a very low water content azeotrope), allows the recovery of water by use of a decanter, even in the presence of unreacted alcohols.

According to the present invention, water is permissible in the propanol feedstocks A2 to be dehydrated; the said feedstock may comprise up to 50 wt % of water, but preferably the said feedstock comprises less than 25 wt % of water, and most preferably the feedstock comprises less than 20 wt % of water. However due to processing costs such as the reactor size, heat of vaporization and heat capacity of water, it is preferred to operate with feedstocks containing lower levels of water for example less than 10 wt %, preferably less than 5 wt % of water. When Heteropolyacids are used as catalysts the level of water in contact with the catalyst can affect the catalyst stability and activity. For example heteropolyacids show a diminished catalyst stability at low levels of water (<1 wt %) and a diminished activity at high levels of water (>50 wt %). To one skilled in the art it is apparent that the optimum water level will depend on the interaction of a complex set of variables including, alcohol feed composition, pressure, temperature and nature of the heteropolyacid employed. That said, this process has a good ability to separate water out and hence facilitates the use of bioethanol and other bioalcohol(s). The operation at medium conversion with water removal during recycle has the advantage in that it allows convergence towards the optimum reaction conditions of the process. The presence of water in the feed can also increase the difficulty of the alcohol separation due to the presence of alcohol water azeotropes which serves to narrow the boiling point difference for separation.

According to the most preferred embodiment of the present invention the propanol and propyl ethers together with the water represent at least 90 wt % and preferably at least 99 wt % of the feedstock A2 introduced into vapour phase dehydration reactor.

Additional sources of propanol can be added to either the alcohol separation column or directly to the reactor feeds e.g. bio-propanol to stream A2.

The vapour phase reactor used for dehydrating the propanol feedstock A2 according to the present invention is preferably operated at a temperature comprised between 160 and 270° C., preferably between 180 and 270° C., more preferably between 190 and 240° C. and most preferably between 200 and 225° C.

The vapour phase reactor used for dehydrating the propanol feedstock A2 according to the present invention is preferably operated at a pressure of above 0.1 MPa but less than 4.5 MPa, preferably above 0.15 MPa but less than 4.0 MPa, and most preferably more than 1.0 MPa but less than 2.0 MPa.

According to the present invention the operating conditions are such that the dehydration process is always operated in a vapour phase state. It is a preferred embodiment that the dehydration process operating pressure is always at least 0.1 MPa, preferably 0.2 MPa, below the dew point pressure and/or that the dehydration process operating temperature is at least 10° C. above the dew point temperature of the feed entering the vapour phase dehydration reactor (the alcohol feed mixture and/or the mixture resulting from addition of the recycle) and the product composition that is present inside the dehydration reactor. The latter will depend on factors such as the initial feed composition and the degree of conversion in the reactor.

For the purposes of the present invention, the 'dew point temperature' is defined as being a threshold temperature. For example, for a given mixture, at a given pressure, if the system temperature is raised to above the dew point temperature, the mixture will exist as a dry gas. Likewise below the dew point temperature, the mixture will exist as a vapour containing some liquid. And similarly the 'dew point pressure', is defined as being a threshold pressure. For example, for a given mixture, at a given temperature, if the system pressure is below the dew point pressure, the mixture will exist as a dry gas; above the dew point pressure, the mixture will exist as a vapour containing some liquid.

The reactors are engineered to cope with the exothermic ether formation and the endothermic dehydration to olefins. The reaction temperature is preferably maintained within a small temperature range, as too low a temperature reduces the rate of olefin manufacture and can lead to condensation of reactants and too high a temperature can lead to die olefin being contaminated by unacceptable levels of by-products such as same carbon number alkanes. Preferably the temperature profile of the catalyst bed is less than 30 C more preferably less than 15 C and most preferably less than 10 C. For a single bed adiabatic reactor the overall endothermic reaction if allowed to go to thermodynamic equilibrium could result in a theoretical temperature drop of 180 C. Obviously the problem is one of heat management by reactor design. Suitable reactor designs include those capable of handling heat fluxes such as fixed bed, fluidised bed, multitubular and multiple fixed bed reactors with inter stage heaters. Optionally the heat management can be improved by injecting preheated fresh alcohol feed at several points in the reactor bed, at which point the exothermic etherification reaction can partially counteract the overall endotherm. The feed can also be heated further to above the reaction temperature, in order to provide an additional source of heat. A portion of die recycle stream also can be added at several points along the reactor with additional heating but it is preferred to add the main proportion of this stream to the front end of the reactor.

According to an embodiment of the present invention, the dehydration process, described by the present invention, is not conducted in a reactive distillation column. Where a "reactive distillation column" refers to a combined distillation column and reactor.

Surprisingly it has been found by the applicants, that the use of a mixed ether and alcohol feed results in a higher yield and selectivity to olefins. This surprising discovery has shown that operating the process of the present invention with a recycle is advantageous to the productivity and selectivity of die olefin production process. In addition to this, the option of conducting the separate etherification on the alcohol feedstock prior to dehydration is also one embodiment of this invention.

Thus, according to a preferred embodiment of the present invention, the propanol feedstock A2 comprises at least 10 wt %, preferably at least 15 wt %, preferably at least 30 wt %, and most preferably at least 50 wt % ethers but less than or equal to 85 wt % ethers. Said ethers are preferably propanol derived ether(s) such as di n-propyl ether, n-propyl isopropyl ether, and di iso-propyl ether. Said ethers can be produced during the dehydration stage, during the alcohols synthesis stage, during a separate etherification additional stage or simply added to the feedstock(s).

A preferred characterizing feature according to the present invention is that feedstock A2 comprises less than 5 wt %, preferably less than 1 wt % and most preferably less than 0.1 wt % of C1 ethers (e.g. methyl ethyl ether, methyl propyl ether), and/or di-ethyl ethers, and/or C3+ (defined as having at least one 4 carbon atom chain e.g. n-butyl ethyl ether, butyl propyl ether) derived ethers; and ideally contains no C1 ethers and/or di-ethyl ethers, and/or C3+ derived ethers.

According to another embodiment of die present invention, the presence of aldehydes in the oxygenates feedstock and/or the feedstock A2 has been found to be detrimental to the catalyst lifetime. Accordingly the aldehydes content in the said feedstocks is preferably less than 1 wt %, more preferably less than 0.1 wt %. In order to achieve the required absence of aldehydes, it is preferred to remove the said aldehydes from the alcohols feedstocks to be dehydrated by subjecting the said alcohols feedstocks to any one of tire following treatments: a bisulphite wash: a borohydride hydrogenation, a hydrogen hydrogenation or a distillation treatment. The distillation treatment can be combined with a chemical treatment such as caustic catalysed Aldol condensation or borohydride treatment to improve its efficiency for aldehyde removal. The dehydration reaction may also produce small quantities of aldehydes which can be preferably similarly removed by treatment.

According to another embodiment of the present invention, the oxygenates feedstock and/or the feedstock A2 and/or the recycle streams should preferably be substantially free of volatile bases and metal ions which can cause catalyst deactivation. Transition metals ions such as common corrosion metals e.g. Cu, Fe and Ni, can also catalyze hydrogen transfer reactions and lead to loss of quality of the olefin streams due to increased aldehyde and alkane make. Volatile amines can be conveniently removed by treatments such as distillation and/or use of guard beds (typically acidic ion-exchange resin beds). Metal ions can also be conveniently removed by the use of guard beds but careful design of the feed and vaporization unit(s) can afford significant protection.

Olefins such as ethylene and propylene used in polymer manufacture by virtue of the high activity and turnover numbers of the catalysts employed for polymerisation are susceptible to the presence of low amounts of impurities; these can be removed by well known treatments for the olefin. Alternatively some of these impurities such as sulphur compounds which may be present in bio-ethanol can be removed by pre-treatment of the feedstock.

According to a preferred embodiment of the present invention the alcohols present in the oxygenates feedstock are transported from a remote location prior to being separated and dehydrated to olefin(s) via the above process. For the purpose of this invention and the appending claims the term 'remote location' refers to a location that is more than 100 kilometers from the alcohol dehydration units.

According to a preferred embodiment of the present invention the catalyst used for the dehydration of the propanol feedstock A2 are heterogeneous catalyses). It includes but is not limited to heteropolyacids, sulphonated supports (e.g. Nation and ion exchange resins, Sulphonated zirconia, Pt sulphonated zirconia), Niobia, phosphoric acid on silicaceous supports (silica, Kieselguhr, clays), zeolites, metal modified zeolites, mordenites and mixtures thereof; preferably heteropolyacids and ion-exchange resins; more preferably heteropolyacids; and most preferably 12-tungstosilicic acid, 12-tungstophosphoric acid, 18-tungstophosphoric acid and 18-tungstosilicic acid and partial salts thereof.

The term "heteropolyacid", as used herein and throughout the description of the present invention, is deemed to include inter alia; alkali, alkali earth, ammonium, free acids, bulky cation salts, and/or metal salts (where the salts may be either full or partial salts) of heteropolyacids. Hence, the heteropolyacids used in the present invention are complex, high molecular weight anions comprising oxygen-linked polyvalent metal atoms. Typically, each anion comprises 12-18, oxygen-linked polyvalent metal atoms. The polyvalent metal atoms, known as peripheral atoms, surround one or more central atoms in a symmetrical manner. The peripheral atoms may be one or more of molybdenum, tungsten, vanadium, niobium, tantalum, or any other polyvalent metal. The central atoms are preferably silicon or phosphorus, but may alternatively comprise any one of a large variety of atoms from Groups I-VIII in the Periodic Table of elements. These include copper, beryllium, zinc, cobalt, nickel, boron, aluminium, gallium, iron, cerium, arsenic, antimony, bismuth, chromium, rhodium, silicon, germanium, tin, titanium, zirconium, vanadium, sulphur, tellurium, manganese nickel, platinum, thorium, hafnium, cerium, arsenic, vanadium, antimony ions, tellurium and iodine. Suitable heteropolyacids include Keggin, Wells-Dawson and Anderson-Evans-Perloff heteropolyacids. Specific examples of suitable heteropolyacids are as follows:

| | |
|---|---|
| 18-tungstophosphoric acid | $H_6[P_2W_{18}O_{62}] \cdot xH_2O$ |
| 12-tungstophosphoric acid | $H_3[PW_{12}O_{40}] \cdot xH_2O$ |
| 12-molybdophosphoric acid | $H_3[PMo_{12}O_{40}] \cdot xH_2O$ |
| 12-tungstosilicic acid | $H_4[SiW_{12}O_{40}] \cdot xH_2O$ |
| 12-molybdosilicic acid | $H_4[SiMo_{12}O_{40}] \cdot xH_2O$ |
| Cesium hydrogen tungstosilicate | $Cs_3H[SiW_{12}O_{40}] \cdot xH_2O$ | and the free acid or partial salts of the following heteropolyacids:

| | |
|---|---|
| Monopotassium tungstophosphate | $KH_5[P_2W_{18}O_{62}] \cdot xH_2O$ |
| Monosodium 12-tungstosilicic acid | $NaK_3[SiW_{12}O_{40}] \cdot xH_2O$ |
| Potassium tungstophosphate | $K_6[P_2W_{18}O_{62}] \cdot xH_2O$ |
| Sodium molybdophosphate | $Na_3[PMo_{12}O_{40}] \cdot xH_2O$ |
| Ammonium molybdodiphosphate | $(NH_4)_6[P_2Mo_{18}O_{62}] \cdot xH_2O$ |
| Potassium molybdodivanado phosphate | $K_5[PMoV_2O_{40}] \cdot xH_2O$ |

In addition mixtures of different heteropolyacids and salts can be employed The preferred heteropolyacids for use in die process described by the present invention is any one or more heteropolyacid that is based on the Keggin or Wells-Dawson structures; more preferably the chosen heteropolyacid for use in the process described by the present invention is any one or more of the following: silicotungstic acid, phosphotungstic acid, silicomolybdic acid and phosphomolybdic acid; and most preferably the chosen heteropolyacid for use in the process described by the present invention is any one or more silicotungstic acid.

The heteropolyacids employed according to the present invention may have molecular weights of more than 700 and less than 8500, preferably more, than 2800 and less than 6000. Such heteropolyacids also include dimeric complexes.

The supported catalyst may be conveniently prepared by dissolving the chosen heteropolyacid in a suitable solvent, where suitable solvents include polar solvents such as water, ethers, alcohols, carboxylic acids, ketones and aldehydes; distilled water and/or ethanol being the most preferable solvents. The resulting acidic solution has a heteropolyacid concentration that is preferably comprised between 10 to 80 wt %, more preferably 20 to 70 wt % and most preferably 30 to 60 wt %. This said solution is then added to the chosen support (or alternatively the support is immersed in the solution). The actual volume of acidic solution added to the support is not restricted, and hence may be enough to achieve incipient wetness or wet impregnation, where wet impregnation (i.e. preparation using an excess acidic solution volume relative to pore volume of support), is the preferred method for the purposes of the present invention.

The resulting supported heteropolyacid may be modified, and various salts of heteropolyacid may then be formed in the aqueous solution either prior to, or during, impregnation of the acidic solution onto the support, by subjecting the supported heteropolyacid to a prolonged contact with a solution of a suitable metallic salt or by addition of phosphoric acid and/or other mineral acids.

When using a soluble metallic salt to modify the support, the salt is taken in the desired concentration, with the heteropolyacid solution. The support is then left to soak in the said acidic solution for a suitable duration (e.g. a few hours), with periodic stirring or shaking, after which time it is filtered, using suitable means, in order to remove any excess acid.

When the salt is insoluble it is preferred to impregnate the catalyst with the HPA and then tritrate with the salt precursor. This method can improve the dispersion of the HPA salt Other techniques such as vacuum impregnation may also be employed.

The impregnated support may men be washed and dried. This may be achieved using any conventional separation technique, including, for example, decantation and/or filtration. Once recovered, the impregnated support may be dried, preferably by placing the support in an oven at elevated temperature. Alternatively, or additionally, a desiccator may be employed. On a commercial scale this drying stage is often achieved by a purge of hot inert gas such as nitrogen.

The amount of heteropolyacid impregnated on the resulting support is suitably in the range of 10 wt % to 80 wt % and preferably 20 wt % to 50 wt % based on the total weight of the heteropolyacid and the support.

The weight of the catalyst on drying and the weight of the support used, may be used to obtain the weight of the acid on the support by deducting the latter from the former, giving the catalyst loading as 'g heteropolyacid/kg catalyst'. The catalyst loading in 'g heteropolyacid/litre support' can also be calculated by using the known or measured bulk density, of the support. The preferred catalytic loading of heteropolyacid is 150 to 600 g HPA/kg Catalyst It should be noted mat the polyvalent oxidation states and hydration states of the heteropolyacids stated previously and as represented in the typical formulae of some specific compounds only apply to the fresh acid before it is impregnated onto the support, and especially before it is subjected to the dehydration process conditions. The degree of hydration of the heteropolyacid may affect the acidity of the supported catalyst and hence its activity and selectivity. Thus, either or both of these actions of impregnation and dehydration process may change the hydration and oxidation state of the metals in the heteropolyacids, i.e. the actual catalytic species used, under the process conditions given, may not yield the hydration/oxidation states of the metals in the heteropolyacids used to impregnate the support. Naturally therefore it is to be expected that such hydration and oxidation states may also be different in the spent catalysts after reaction.

Suitable catalyst supports may be in a powder form or may be granules, pellets, spheres or extrudates and include, but are not limited to, Mordenites e.g. montmorillonite, clays, bentonite, diatomous earth, titania, activated carbon, alumina, silica-alumina, silica-titania cogels, silica-zirconia cogels, carbon coated alumina, zeolites, zinc oxide, flame pyrolysed oxides. Supports can be mixed oxides, neural or weakly basic oxides. Silica supports are preferred, such as silica gel supports and supports produced by the flame hydrolysis of $SiCl_4$. Preferred supports are substantially free of extraneous metals or elements which might adversely affect the catalytic activity of the system. Thus, suitable silica supports are at least 99% w/w pure. Impurities amount to less than 1% w/w, preferably less than 0.60% w/w and more preferably less than 0.30% w/w. The pore volume of the support is preferably more man 0.50 ml/g, preferably more man 0.8 ml/g. The average pore radius (prior to use) of the support is 10 to 500 Å, preferably 30 to 175 Å, more preferably 50 to 150 Å and most preferably 60 to 120 Å. The BET surface area is preferably between 50 and 600 m2/g and is most preferably between 150 and 400 m2/g. The support has an average single particle crush strength of at least 1 kg force, suitably at least 2 kg force, preferably at least 6 kg force and more preferably at least 7 kg force. The bulk density of the support is at least 380 g/l, preferably at least 395 g/l.

The single particle crush strength was determined by using a Mecmesin force gauge which measures the minimum force necessary to crush a particle between parallel plates. The crush strength is based on the average of that determined for a set of 50 catalyst particles.

The BET surface area, pore volume, pore size distribution and average pore radius were determined from the nitrogen adsorption isotherm determined at 77K using a Micromeritics TRISTAR 3000 static volumetric adsorption analyser. The procedure used was an application of British Standard methods BS4359: Part 1:1984 'Recommendations for gas adsorption (BET) methods' and BS7591-Part 2:1992, 'Porosity and pore size distribution of materials'—Method of evaluation by gas adsorption. The resulting data were reduced using the BET method (over the pressure range 0.05-0.20 P/Po) and the Barrett, Joyner & Halenda (BJH) method (for pore diameters of 20-1000 Å) to yield the surface area and pore size distribution respectively.

Suitable references for the above data reduction methods are Brunauer, S, Emmett, P H, & Teller, E, J. Amer. Chem. Soc. 60, 309, (1938) and Barrett, E P, Joyner, L G & Halenda P P, J. Am. Chem. Soc., 1951 73 373-380.

Samples of the supports were out gassed for 16 hours @120° C. under a vacuum of 5×10-3 Torr prior to analysis.

Suitable silica supports include, but are not limited to, GraceDavison G57, GraceDavison 1252, Grace Davison 1254, Fuji Silysia CariAct Q15, Fuji Silysia CariAct Q10, Aerolyst 3045 and Aerolyst 3043. The average diameter of the support particles is 2 to 10 mm, preferably 3 to 6 mm. However, these particles may be crushed and sieved to smaller sizes of, for example, 0.5-2 mm, if desired.

A further embodiment of the said invention is where the chosen catalyst support is first treated with a fluorinating agent; the applicants believe that by fulfilling this said embodiment the catalyst will become more inert and/or acidic thus improving the selectivity and/or effectiveness of the catalyst during the aforementioned dehydration process.

FIG. 1 represents one embodiment of a process scheme according to the present invention. This said embodiment comprises optional and/or preferred process steps awarding to the present invention.

The letters used to depict the respective feedstocks/product streams correspond to the definitions given in the above text and appending claims.

The invention claimed is:

1. Process for the production of propylene from a propanol feedstock A2 comprising the following steps:
   1. reacting the propanol feedstock A2 in a vapour phase dehydration reactor wherein the propanol is converted at a temperature comprised between 160 and 270° C. and at a pressure of above 0.1 MPa but less than 4.5 MPa, into a product stream B2 comprising propylene, propyl ethers, water and unconverted and/or isomerised propanols,
   2. cooling said product stream B2,
   3. disengaging said cooled product stream B2 in a separation unit to give a first stream C2 comprising propylene and propyl ethers, and a second product stream D2 comprising water, propyl ethers and unconverted and/or isomerised propanols,
   4. feeding said product stream D2 to a dewatering unit wherein a water stream F2 is separated from a propyl ethers and unconverted and/or isomerised propanols stream E2,
   5. recycling said stream E2 into the dehydration reactor of step 1,
   6. cooling said product stream C2,
   7. feeding said cooled product stream C2 to a purification unit wherein a propyl ethers stream G2 is separated from a propylene stream H2, and
   8. optionally, recycling the propyl ethers stream G2 to either the dewatering unit of step 4 or directly to dehydration reactor of step 1, wherein the propanol feedstock A2 comprises at least 10 wt % but less than or equal to 85 wt % ethers; said ethers being selected from the group consisting of di n-propyl ether, n-propyl isopropyl ether and di iso-propyl ether.

2. Process according to claim 1 wherein the propanol feedstock A2 comes from the separation of a mixed ethanol and propanol oxygenates feedstock.

3. Process for the conversion of hydrocarbons to propylene comprising the steps of:
   a. converting in a syngas reactor hydrocarbons into a mixture of carbon oxide(s) and hydrogen,
   b. converting the said mixture of carbon oxide(s) and hydrogen from step (a) in the presence of a particulate catalyst in a reactor under a temperature comprised between 200 and 400° C. and a pressure of 5 to 20 MPa into a feedstock comprising propanol,
   c. using at least part of said feedstock comprising propanol as the propanol feedstock A2 and proceeding according to steps 1 to 8 of claim 1 to produce the said propylene.

4. Process according to claim 1 wherein the propanol feedstock A2 has an iso-propanol content of less than 5 wt %.

5. Process according to claim 1 wherein the propanol feedstock A2 has a C3+ alcohols content of less than 5 wt %.

6. Process according to claim 1 wherein the propanol feedstock A2 has a methanol content of less than 5 wt %.

7. Process according to claim 1 wherein the feedstock A2 comprises less than 5 wt % of ethanol.

8. Process according to claim 1 wherein the propanol, the propyl ethers and the water represent at least 90 wt % of the propanol feedstock A2 introduced into the vapour phase dehydration reactor.

9. Process according to claim 1 wherein the propanol feedstock A2 comprises less than 5 wt % of C1 ethers, and/or di-ethyl ethers, and/or C3+ derived ethers.

10. Process according to claim 4 wherein the iso-propanol content is less than 1 wt %.

11. Process according to claim 4 wherein the iso-propanol content is less than 0.1 wt %.

12. Process according to claim 4 wherein the propanol feedstock A2 contains no iso-propanol.

13. Process according to claim 5 wherein the propanol feedstock A2 has a C3+ alcohols content of less than 1 wt %.

14. Process according to claim 5 wherein the propanol feedstock A2 has a C3+ alcohols content of less than 0.1 wt %.

15. Process according to claim 5 wherein the propanol feedstock A2 contains no C3+ alcohols.

16. Process according to claim 6 wherein the propanol feedstock A2 has a methanol content of less than 2 wt %.

17. Process according to claim 6 wherein the propanol feedstock A2 has a methanol content of less than 0.5 wt %.

18. Process according to claim 6 wherein the propanol feedstock A2 contains no methanol.

19. Process according to claim 7 wherein the feedstock A2 comprises less than 1 wt % of ethanol.

20. Process according to claim 7 wherein the feedstock A2 comprises less than 0.1 wt % of ethanol.

21. Process according to claim 7 wherein the feedstock A2 contains no ethanol.

22. Process according to claim 8 wherein the propanol, the propyl ethers and the water represent at least 99 wt % of the propanol feedstock A2 introduced into the vapour phase dehydration reactor.

23. Process according to claim 1 wherein the propanol feedstock A2 comprises at least 15 wt % ethers.

24. Process according to claim 1 wherein the propanol feedstock A2 comprises at least 30 wt % ethers.

25. Process according to claim 1 wherein the propanol feedstock A2 comprises at least 50 wt % ethers.

26. Process according to claim 9 wherein the propanol feedstock A2 comprises less than 1 wt % of C1 ethers, and/or di-ethyl ethers, and/or C3+ derived ethers.

27. Process according to claim 9 wherein the propanol feedstock A2 comprises less than 0.1 wt % of C1 ethers, and/or di-ethyl ethers, and/or C3+ derived ethers.

28. Process according to claim 9 wherein the propanol feedstock A2 contains no C1 ethers and/or di-ethyl ethers, and/or C3+ derived ethers.

\* \* \* \* \*